(12) United States Patent
Fritz Zuñiga et al.

(10) Patent No.: US 9,924,714 B2
(45) Date of Patent: Mar. 27, 2018

(54) IMPREGNATABLE MATRIX OF PLANT, ANIMAL OR SYNTHETIC ORIGIN OR MIXTURES OF SAME, CONTAINING A UNIFORMLY DISTRIBUTED ANTIMICROBIAL COMPOUND, METHOD FOR IMPREGNATING SAID MATRIX WITH A COMPOUND, AND USE THEREOF IN THE PRODUCTION OF ANTIMICROBIAL ELEMENTS

(71) Applicant: COMPAÑIA MINERA SAN GERONIMO, Coquimbo, IV Region (CL)

(72) Inventors: Hans Reginaldo Fritz Zuñiga, Coquimbo (CL); Javier Ignacio Lavin Carrasco, Coquimbo (CL)

(73) Assignee: COMPAÑIA MINERA SAN GERONIMO, Coquinbo, IV Region, OT (CL)

( * ) Notice: Subject to any disclaimer, the term of this patent is extended or adjusted under 35 U.S.C. 154(b) by 0 days.

(21) Appl. No.: 14/765,205

(22) PCT Filed: Jan. 29, 2014

(86) PCT No.: PCT/CL2014/000004
§ 371 (c)(1),
(2) Date: Jul. 31, 2015

(87) PCT Pub. No.: WO2014/117286
PCT Pub. Date: Aug. 7, 2014

(65) Prior Publication Data
US 2015/0359216 A1    Dec. 17, 2015

(30) Foreign Application Priority Data
Feb. 1, 2013    (CL) .................................... 332-2013

(51) Int. Cl.
*A61K 9/14*   (2006.01)
*A01N 25/08*   (2006.01)
*A01N 59/20*   (2006.01)
*D06M 16/00*   (2006.01)
*D06M 10/06*   (2006.01)

(52) U.S. Cl.
CPC ............. *A01N 25/08* (2013.01); *A01N 59/20* (2013.01); *D06M 10/06* (2013.01); *D06M 16/00* (2013.01)

(58) Field of Classification Search
None
See application file for complete search history.

(56) References Cited

U.S. PATENT DOCUMENTS

| | | | |
|---|---|---|---|
| 5,458,906 A | 10/1995 | Liang | |
| 2007/0190175 A1* | 8/2007 | Cummins | A61K 8/23 424/618 |
| 2008/0051911 A1* | 2/2008 | Rucker | A61F 2/04 623/23.7 |

FOREIGN PATENT DOCUMENTS

| | | |
|---|---|---|
| EP | 0799928 A2 | 10/1997 |
| JP | 2000-118585 A | 4/2004 |

OTHER PUBLICATIONS

English Translation of JP 2000-118585 published Apr. 25, 2004.
International Search Report from PCT/CL2014/000004 dated May 21, 2014.
English Translation of International Search Report from PCT/CL2014/000004 dated May 21, 2014.
Written Opinion of the International Searching Authority from PCT/CL2014/000004 dated May 21, 2014.
English Translation of Written Opinion of the International Searching Authority from PCT/CL2014/000004 dated May 21, 2014.
International Preliminary Report no Patentability from PCT/CL2014/000004 dated Aug. 4, 2015.

* cited by examiner

*Primary Examiner* — Susan Tran
(74) *Attorney, Agent, or Firm* — DLA Piper LLP (US); Gianni Minutoli

(57) ABSTRACT

An impregnable matrix of plant, animal or synthetic origin or mixtures of same in different proportions, containing an antimicrobial compound uniformly distributed throughout the whole composition, in which the compound is a compound of a transition metal, particularly $Cu_4SO_4(OH)_6$. In addition, a method is provided for impregnating the matrix with a compound, comprising steps of (a) absorbing or impregnating the antimicrobial compound; (b) centrifuging or pressing or crushing; (c) air drying; and (d) binding and obtaining the active principle. Moreover, the use of the method for the preparation of a matrix having antimicrobial properties and the use of the matrix in the preparation of solid supports or solid materials for cosmetic, pharmaceutical, medical or veterinary use are provided.

11 Claims, 3 Drawing Sheets

Figura 1.

1.a)

1.b)

Figura 2.

2.a)

2.b)

Figura 3.

3.a)

3.b)

IMPREGNATABLE MATRIX OF PLANT, ANIMAL OR SYNTHETIC ORIGIN OR MIXTURES OF SAME, CONTAINING A UNIFORMLY DISTRIBUTED ANTIMICROBIAL COMPOUND, METHOD FOR IMPREGNATING SAID MATRIX WITH A COMPOUND, AND USE THEREOF IN THE PRODUCTION OF ANTIMICROBIAL ELEMENTS

CROSS REFERENCE TO RELATED APPLICATIONS

This application is a U.S. National Stage Application of International Application No. PCT/CL2014/000004 filed Jan. 29, 2014, which claims priority from CL Patent Application No. 332-2013 filed Feb. 1, 2013. The entirety of all the above-listed applications are incorporated herein by reference.

The present invention consists of a matrix containing a compound of a transition metal which confers antimicrobial properties and a method for incorporating said compound of a transition metal in a matrix of animal, vegetable or synthetic origin, with a uniform distribution and with high level of fixation.

The present invention relates more particularly to a matrix containing a copper compound, which confers antimicrobial properties to the matrix. The present invention also relates to a method for incorporating this copper compound to the matrix.

The incorporation of particles of compounds containing transition metals, mainly copper and silver, to solid matrices, such as a fabric or leather, is commonly done through copper particles or copper wires, where the metal is at zero state, i.e., metallic state, so it must be oxidized to release and activation and thus act as an antimicrobial agent. At the same time, products presenting copper wires as part of its internal structure do not provide concentration gradients of antimicrobial agent that feature activity on one side of the matrix and not on the other.

In the state of the art, there are some solutions to deliver antimicrobial properties to different surfaces using copper, this by macro dispersion, which generally has low effectiveness.

The document U.S. Pat. No. 8,183,167 (B1) of 2012, they are submitted substrates for fabrics which exhibit antimicrobial properties and/or antifungal which persist through the life of the substrate, and more particularly to textile substrates infused with, or covalently bonded to, antimicrobial or dispersed nanoparticles, such as silver and/or copper nanoparticles, which exhibit bactericidal bacteriostatic capabilities, with fungicidal fungistatic behavior through many wash cycles. Production methods of such substrates are also presented. One of the claims indicates that it is a substrate for 1% of synthetic polymer fiber for textiles.

The present invention differs from the solution proposed in U.S. Pat. No. 8,183,167 (BI), given that it is not required to control the size of particles to be incorporated into the matrix, and furthermore, the present invention is directed to matrixes of natural origin, on the contrary, the solution proposed in U.S. Pat. No. 8,183,167 (BI) is directed to synthetic polymers. Additionally, the process proposed by the present invention is a procedure where a number of physical stages are used for fixing the product, which confers antimicrobial properties, as the compound is incorporated into the matrix homogeneously.

The document U.S. Pat. No. 8,105,635 of 2010 describes post-treatment compositions and methods useful for changing the distribution of metal biocide in biodegradable substrates such as wood, other cellulosic products, starch based products, and the like that are vulnerable to decay due to insects, fungi, microbes and the like. In this document, it is claimed a method for treating biodegradable substrates with biocide compounds such as copper.

U.S. Pat. No. 7,754,625B2 of 2010 describes an antimicrobial textile comprising one or more natural or synthetic fibers or filaments having associated therewith an antimicrobial agent, wherein said antimicrobial agent comprises a predominant amount of a soluble zinc salt in water in combination with at least one source of antimicrobial silver ions and at least one source of copper ions, which can be of the same source as the source of silver ions.

The document US 2008/0311165 (AI) of 2005 describes a method for treating and curing ulcers, cold sores, cutaneous openings, ulcerations, lesions, abrasions, burns and skin diseases, which comprises applying to a surface of its exhibited body, a material incorporating water in soluble copper compounds which release Cu+ ions, Cu++ ions or combinations thereof upon contact with a fluid to make the treatment and healing thereof effective.

Herein it is indicated that the material is a fabric having water-insoluble fibers incorporating copper compounds. The fibers are coated with copper compounds. In the process of generation of the fiber, raw material is heated from 120 to 180° C. and the copper oxide is added.

Meanwhile, in document U.S. Pat. No. 7,169,402B2 2007, it is disclosed an antimicrobial and antiviral polymeric material having microscopic particles of ionic copper encapsulated therein and protruding from surfaces thereof.

Antimicrobial and antiviral polymeric material is disclosed, comprising a polymer selected from the group consisting of polyamide, polyester and polypropylene, and one anti-microbial and anti-viral component, consisting essentially of microscopic particles of copper oxide insoluble in water incorporated in the polymer, wherein a portion of the particles in said polymer are exposed and protrude from the material surface.

The document U.S. Pat. No. 4,201,825 of 1998 relates to a metallized textile. The invention also relates to a process for producing such a metallized fabric by deposition of metal (copper, nickel) without current, preferably at room temperature where the activation of the material is effected in a solution of colloidal palladium, preferably at room temperature.

Wherein, the metal is present in the fabric in a coating of at least 0.3 µm thick. The coating is added through metal salt baths, preferably bath of nickel salts, cobalt salts or mixtures thereof, copper salts, gold salts or other salts that can be deposited from alkaline baths.

In U.S. Pat. No. 7,296,690B2 of 2007, it is described a device for inactivating a virus comprising a housing delimiting a fluid conduit, wherein the conduit is provided with a filter material having ionic copper selected from the group consisting of Cu+ and Cu++ ions and combinations of them incorporated. The device has a filter with copper powder or associated with fibers.

The document U.S. Pat. No. 7,364,756B2 2008, describes a method to confer antiviral properties to a hydrophilic polymer, which comprises preparing a hydrophilic polymer suspension. In this hydrophilic material, it is added a mixture of water insoluble particles that release both Cu++ and Cu+, wherein said particles are in proportions 1 to 3% w/w in the material. The hydrophilic material (such as that used for manufacturing disposable gloves and/or male condoms) is cured as it passes through different areas of the oven and is exposed to temperatures ranging from about 120 to 140° C. This cross-linking process bonds the rubber latex to impart the required physical qualities. The difference between the normal process of manufacturing a disposable material and this document method is that in the latest, it is added insoluble particles containing ions Cu++ and Cu+ which are then released into raw materials. The document U.S. Pat. No. 5,405,644 of 1995 describes a process for producing a fiber having a microbicide inorganic antimicrobial containing silver, characterized by using a treatment solution for producing the fiber containing a discoloration inhibitor. The method for supporting silver has no particular restriction. The supporting method can be exemplified by a method comprising kneading a resin that was made into a fiber and a microbicide and subjecting the mixture to spinning, and a method which comprises applying a microbicide mixed with a binder, to the surface of a fiber spun by coating, dipping or similar.

The document U.S. Pat. No. 5,399,425 of 1992 describes a method using polymer substrate (NHRCO—a polymer having at least one repeating unit) and it is first treated with a solution of a strong base to generate anionic surface sites. The treated structure is put in contact with a solution of metal cation (group 8 to 12 periodic table) desired adhering to it through ion exchange. The process of the invention can be performed at temperatures between 17° C. to 190° C. The preferred temperature is room temperature about 60° C. The process may be more conveniently performed at a subatmospheric pressure of 35,000 psig.

The patent W09806508 of 1999 describes a process for the activation of a textile to catalyze the reduction of a metal cation (Cu, Ag, Zn, Ni, CuO, $Ag_2O$, ZnO and NiO), a metallization process for textile. The textile is immersed in a properly prepared solution of a metal cation and adding a reducing agent; this leads to the formation of a sealed metal coating and intimately bonded to the fibers of the fabric.

The document W09806509 (AI) of 1998 describes the use of metallized textile. The textile is activated precipitating nucleation sites of a noble metal on the textile fibers. The method comprises the steps of:

(a) providing a metallized textile, the metallized textile comprising: (i) a fabric including selected fibers from the group consisting of natural fibers, synthetic fibers, regenerated cellulosic fibers, acrylic fibers, polyolefin fibers, polyurethane fibers, vinyl fibers and fiber mixtures of them, and (ii) a plating including materials selected from the group consisting of metals and metal oxides, the metallized textile characterized in that the lining is directly bonded to the fibers and (b) incorporating the metallized textile in an article of manufacture.

The same process described above, is mentioned in other patents and prior art, with reference to W09806509. In these cases, the procedure is described according to the following steps: a) selecting a textile, in a form selected from the group consisting of yarn and fabric, said textile including fibers selected from the group consisting natural fibers, synthetic cellulosic fibers, regenerated protein fibers, acrylic fibers, polyolefin fibers, polyurethane, vinyl fibers, and mixtures of them; b) soaking said textile in a solution containing at least one reducing cationic species having at least two positive oxidation states; c) soaking said textile in a solution containing at least one kind of noble metal cation, thereby producing an activated textile, and d) reducing at least one oxidant cationic species in a medium in contact with said active textile, thereby producing a textile metallic.

The document W00075415 (AI) of 2000 introduces an article about clothing having antibacterial and antifungal, comprising at least one panel of a textile (natural fibers, synthetic cellulosic fibers, regenerated protein fibers, acrylic fibers, polyolefin fibers, polyurethane fibers, vinyl fibers, and blends of them) and having a coating including antibacterial and antifungal effective amount of at least one oxidant cationic species of copper. In this document, there are two steps shown in the process of production of the fabric: The first step is activation of the textile by precipitating catalytic metal nucleation sites. This is done soaking the textile in a solution of a reducing cation of low oxidation state and then soaking the textile in a solution of noble metal cations, preferably a solution of Pd++, more preferably an acid. The second is a reducing metal cation. The metallized textiles thus produced are characterized because their metallic coating is bonded directly to textile fibers.

The document W09600321 (AI) of 1996 refers to a fiber material used for the production of textile products such as woven fabrics, nonwoven fabric, paper, among others similar. The method for producing an antibacterial fiber comprises the following steps: bonding, through an ion exchange reaction, the complex ion of silver, copper or zinc with the ion of the exchange group of fiber with cation exchange, which has a sulfonic group or a carboxyl group as the ionic exchange group; and then the complex ion is reduced.

The document TW201018762 of 2010 (Taiwan) describes an antibacterial textile with bleaching which includes a textile substrate, an aqueous resin and an antibacterial powder. The surface of the textile substrate is covered with the aqueous resin. The antibacterial powder is distributed in the aqueous resin; said antibacterial powder includes silicon dioxide particles and silver nanoparticles which are synthesized with each other. Additionally, the antibacterial powder and methods of making the aforementioned antibacterial textiles are included in the patent.

The document US2006156948 of 2006 refers to ionic coatings of silver based in antimicrobial, particularly erosive coatings having improved color stability without compromising the level of active antimicrobial silver. In particular, this document is directed to antimicrobial coatings containing agents of ion exchange antimicrobial type, especially zeolites, having excellent antimicrobial properties without discoloration due to the formation of silver compounds. In this document, copper compounds are also mentioned as a substitute for silver ions.

The document W09415463 (AI) of 1994 describes an antimicrobial composition comprising an inorganic particle (copper, silver) with a first coating providing antimicrobial properties and a second coating providing a protective function, the patented method for preparing the composition and its use. Other processes for the production of polymer items and also describes a method for controlling microorganisms. The steps in the present invention are: (a) forming an aqueous suspension of material particles core; (b) depositing a first coating of the desired antimicrobial component or components on the core particle surface with suitable precipitation reactions; (c) depositing a secondary protective silica and/or alumina coating by adding an alkali metal silicate or aluminate to the suspension, keeping the pH, (d) optionally, it is applied a coating of a hydrous metal oxide by treatment of the particles suspended with a salt; (E) recovering the solids, washing free from water soluble species and drying; and (f) optionally adding steam micronization.

The document DE102007048107 (AI) of 2009 (Germany) describes an antibiotically active substrate for seeding purposes in the production of materials such as dyes, papers, clothes, chamfer and materials and supplies, preferably suspensions for surface coatings, comprising active nanomaterial with antibiotic properties; arrangement made from a continuous metallic coating with a highly porous surface or in connection with a porous substrate which forms a corrosion cell where continuous nano-porous metallic surface is formed with a high surface area of silver, copper, zinc, mercury, tin, lead, bismuth, cadmium, chromium and thallium metal as an antimicrobial.

The document W00181671 (A2) of 2001 describes a method for the treatment and prevention of nosocomial infections. This method comprises incorporating into fabrics or textiles used in health, fibers coated with an oxidant as cationic form of copper. Such fabrics may be used in contact with the patient for care or medical use in which the fabric is effective for the inactivation of bacterial strains resistant to antibiotics.

Meanwhile, the document R0117626 (BI) of 2002 (Romania) relates to a process for obtaining cotton fabrics with a metal coating consisting of roughness, wherein said metal is particularly copper. This procedure consists of preparing an alkaline solution comprising 550 g/L of ethylene glycol and 60 g/L of sodium hydroxide, neutralization is carried out subsequently, and it is sensitized with a solution containing hydrazine hydrate, chemically activating the coating metal. The copper plating solution has a mixture of salt, which is fixed electrochemically sodium tellurate.

In the scientific article of the Journal ECI Peru, vol. 8, No. I, January 2011, "Synthesis of nanostructured copper oxide assisted with gamma irradiation or ultrasound and its antimicrobial properties," it is described the synthesis of oxide nanoparticles (CuO) by gamma irradiation or ultrasound. The antimicrobial activity of CuO nanoparticles was determined by the method of excavation in culture plate with 3 microbial strains: *Staphylococcus aureus* ATCC 25923, *Escherichia coli* ATCC 25922 and *Pseudomonas aeruginosa* ATCC 27853. The CuO nanoparticles are nanospheres obtained by ultrasound with a higher antimicrobial activity for *S. aureus* bacteria than for *E. coli* and no activity against *P. aeruginosa*; while CuO nanoparticles obtained with gamma radiation with a dose of 8 kG have antimicrobial activities similar for *S. aureus* and *E. coli*, and those obtained at doses of 15 and 25 kG only have antimicrobial activity against *E. coli*. In this article, the results of CuO nanoparticles impregnated in cotton fabrics are also presented in order to demonstrate its potential use in such matrixes.

DESCRIPTION OF THE INVENTION

The present invention relates to a matrix of animal, vegetable, or synthetic origin or any proportion of the above, containing a compound of a transition metal, particularly copper, where the matrix has antimicrobial properties.

This matrix with antimicrobial properties, or the supporting tissue or material, is impregnated and incorporated with Alkaline Copper Sulfate, formula $Cu_4SO_4(OH)_6$, which corresponds to a molecular rearrangement of copper sulfate pentahydrate $CuSO_4 \cdot 5H_2O$. This alkaline copper sulphate is characterized by a very low solubility and low diffusion when incorporated in the matrix, whereby it is obtained that the matrix maintains its biocide properties even after consecutive washes.

According to the above, the active ingredient is incorporated into the matrix is preferably alkaline copper of formula $(Cu_4SO_4(OH)_6)$, which is an insoluble compound that is obtained from copper sulfate pentahydrate in aqueous ammonia (or ammonium hydroxide) according to the following reactions:

The sulfate of alkaline copper for this invention is preferably obtained from copper sulfate pentahydrate, according to the above mentioned reactions, however, to prepare the solution, it is required the presence of copper cation +2 and sulfate anion −2, therefore, raw materials used may be of any chemical compound containing said cation or anion, either in the same compound, such as copper sulfate, or in different compounds such as copper chloride, copper oxide, copper phosphate, which provides the copper ion with chemical compounds that contribute the sulfate radical as sodium sulfate, potassium sulfate, ammonium sulfate, among others, or copper sulfate in any state of hydration, or a mixture of oxide copper or copper hydroxides neutralized with sulfuric acid.

In the preparation of the active ingredient, it is required the presence of ammonium hydroxide, which is generated from ammonia added to the system in liquid, gaseous form or through form ammonium salts soften with hydroxide salts.

In this process, it is produced a reaction intermediate corresponding to $CuSO_4 \cdot 4NH_3 \cdot H_2O$, from which fixing alkaline copper sulfate $(Cu_4SO_4(OH)_6)$ is obtained by heat treatment. The reaction conditions require a small excess of free ammonia non-ncomplexed in order to ensure the formation of the intermediate compound and minimize other chelation states of copper with ammonia.

Preparation of the Impregnation Solution.

As noted above, it is required to impregnate the matrix with ammonia or ammonia solution, containing a small excess of free ammonia non-ncomplexed, favoring the formation of the intermediate compound once evaporated or exposed to air the excess solution.

The ammonia formula has 5% copper in the solution, which equates to be practice to a 20% copper sulfate pentahydrate plus sufficient ammonia to ensure chelation of copper to form the intermediate compound $CuSO_4 \cdot 4NH_3 \cdot H_2O$.

Impregnation Procedure for Different Matrixes.

The present invention also relates to a method of impregnating copper compounds into a solid animal, vegetable, synthetic or any blend in different proportions among the above materials, which confer antimicrobial properties to said matrix. Such material may be any surface which is permeable to water. Said process allows to obtain a homogeneous distribution of the compound and with different concentrations, independent of the material used, to obtain a desired matrix for various uses.

This procedure can be used on various materials, it being understood as the basis matrix for any surface that allows the incorporation of the compound, such as: fabric (any quality, texture or thickness), paper (any quality, texture or thickness), natural and synthetic leathers (any quality, texture or thickness), or any material containing any proportion of the above materials.

The procedure involves the following steps:
1) Absorption/Impregnation.

In this stage, it is added the ammonium cooper sulphate solution containing the intermediary or other compound containing copper ions and ammonium ions, into the base material in order to form the matrix according to the use requirements of said matrix. This step is intended to incorporate the active ingredient distributed evenly, using the characteristics of the material, such as permeability, capillarity and wetting, to form the matrix.

For preliminary impregnation, the material used shall be immersed for a period to ensure it is completely wet and the distribution of the impregnating solution.

The periods required at this stage are between 5 to 30 minutes, particularly about 10 minutes, and only for standardization, they shall must be verified the desired final copper content. This operation is performed at room temperature (about 20° C.).

2) Spinning/Pressing/Crushing

This stage aims to standardize, delete, and dose much of the excess of the preparation of the dilution, achieving controlled concentrations of the active ingredient (copper) in the matrix.

It is removed by any mechanical means the surplus of aqueous solution of copper sulfate with ammonia to leave copper concentrations required by the end use of the matrix. The mechanical means to choose can be spinning, pressing or crushing, the choice depends on the characteristics of the material which is being handled to achieve the desired antibacterial matrix.

3) Exposure to Air

At this stage, the exceeding aqueous ammoniacal solution is evaporated over the intermediate compound being $CuSO_4.4NH_3.H_2O$.

The airing is intended to maintain uniform distribution and homogeneity of copper in the matrix, to avoid the existence of localized and uncontrolled migration (e.g., drips, liquid displacement copper displacement in the solution etc.).

4) Fixation and Production of the Active Ingredient

The fixation technique allows adhesion with uniform distribution, also can provide a property with homogeneous concentration gradient from one side to another of the matrix or concentrations focused on different areas of the matrix.

This is achieved by giving adhesion properties to the active substance, alkaline copper sulphate, with temperature application; this temperature application can be of any nature which does not impair fixing substrate of the matrix.

In order to transform the reaction intermediate, copper ammonia sulfate $CuSO_4 4NH_3.H_2O$ into final insoluble alkaline copper sulfate $Cu_4SO_4(OH)_6$ in the desired or required matrix sectors, is required to apply between 50 and 120° C. temperature depending on the base material used to form this matrix and periods will be given according to the degree of resistance of the base material used to form the matrix.

The shorter periods and higher temperatures required to achieve the transformation of the intermediary to set final product, shall be conditional upon the strength, integrity and aesthetics of the resulting base material used.

It is noteworthy that the process described above can be used to fix copper hydroxides or oxides that accomplish the same objective of alkaline copper sulfate, using raw materials hydroxides or oxides of copper plus ammonia in gas or liquid state. With this methodology, it is not obtained nanoparticle distribution, but an incorporation of the compounds into the matrix.

The procedure described above allows the compound to be uniformly occluded inside, outside and between the fibers of the matrix, unlike the nanoparticles distribution technique which leaves interstitial spaces not protected by the active ingredient, which would allow the subsistence probability of pathogenic uncontrolled population.

Figure 1:
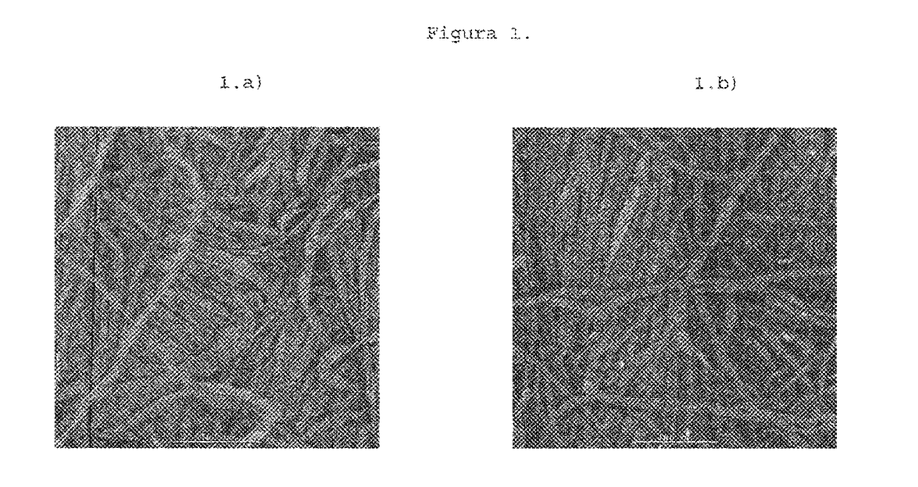
FIG. 1.—Electronic Scanning Microscopy of the fabric with the compound and the control fabric. In a), an image shows the control fabric increased to 160 μm and in b), the picture is taken at the same occluded fixed fabric impregnated with the compound but in an increased size.

FIG. 1 shows how the copper compound is incorporated into the matrix. By electron microscopy, it was determined that all the fibers of the fabric contain a copper compound even when under 16 pm the compound particles cannot be appreciated. It has been determined that the compound molecules are homogeneously distributed in the fibers, which provides antimicrobial properties to the matrix. Furthermore, it allows the uniform distribution of particles in the matrix of the formulation, with different concentration gradients, and can be fixed on only one or both sides of the matrix, or in specific areas of this.

This procedure makes the compound adhere and fix to the matrix, presenting high adhesion, even after washing (home or industrial) and repeated use. The matrix impregnated with alkaline copper sulphate, using this procedure, has antimicrobial properties that act with contact immediately and continuously thanks to its chemical state and distribution. Alkaline copper sulfate is occluded and fixed in the matrix uniformly both inside and outside, and even among the fibers.

The compound, alkaline copper sulphate occluded and fixed to the matrix, is an insoluble precipitate in the presence of humidity (ambient humidity and that of the microorganisms which are in contact with). It leaves free ions which rearranged again into the form of soluble dissociated copper sulfate; process that occurs slowly under control. Said soluble dissociated $CuSO_4$, due to the characteristic of high solubility, leaves immediately cupric ions available in the humid environment, which finally exert the biocidal effect of high activity, which manifests itself in time, in a gradual and controlled manner.

This property of insolubility of the precipitated alkaline copper sulphate doses ions in the medium in the presence of moisture, this dosage is minimal in mass ratio of copper occluded in the matrix, and which ensures durability and permanence in time, even when multiple washes were performed.

The greatest losses will be given by the possible washing of the matrix, but these are minimal in relation to the mass of the fixed and occluded compound. Because of the antimicrobial properties (particularly antibacterial and antifungal properties) that acquires the matrix, it is possible a variety of uses, as the biological properties of the parent applications are combined. Prominent among these uses, but not limited to fabrics, paper, cardboard, leather, among others, with hospital use as blankets, bedding and hospital clothing, bandages and dressings for burned people, bandages and dressings for general use, because the matrix acts as a barrier against pathogens; with anti-odor use for odors produced by microorganisms, such as T-shirts use, sports clothing; antifungals, such as use in matrixes for underwear and socks; use as a disinfectant, for example, wipes or the like; veterinary use, such as in clothing animals; special clothing, such as clothing for diabetics, facial wipes (for example against acne); and others such as fabrics for insoles and shoes; cleaning paper, carpets, mattresses, curtains, sofa, furniture fabric, blankets, jackets, towels, disposable sterilization papers, food container papers based on paperboard, diapers, sanitary towels, garbage bags, paper filters for aeration, purification systems, etc.

Example 1: Preparation of the Impregnation Solution to be Incorporated into a Matrix The formulation is used in dilution with water, the concentration of which depends on the use and characteristics of the matrix to be impregnated. For example, for an array with a final concentration of 3% copper, the calculation is made using the following:

Matrix of dry mass (e.g. cotton fabric): 1000 g.
Copper percentage required in the final matrix occluded 3%
Residual humidity percentage 60% (in the spinning/pressing/crushing stage)
Percentage of copper in the formulated solution 5%

These percentages of moisture in the fabric are obtained after applying the process of the present invention, and are percentages obtained by centrifugation of a 100% cotton fabric.

Antimicrobial Textile Production Process

In the following example was used 1000 g of natural fiber 100% cotton, 400 g of copper sulfate pentahydrate Cu 25%, 1200 ml of water and 25% ammonia, sufficient to dilute to 2000 ml mixture.

Preparation:

In 1200 ml of water, dissolve 400 g of copper sulfate pentahydrate at 25% Cu. Once the crystals are dissolved in water (if necessary, temperature can be applied to achieve full solubilization of solid and then let it cool), and then gauge up to 2000 mL with ammonia solution at 25%. The above mentioned formula is represented by the following chemical equilibrium:

$$CuSO_4 \cdot 5H_2O + 4NH_3 \rightleftharpoons Cu(NH_3)_4^{2+} + SO_4^{2-} + 5H_2O$$

Subsequently, the prepared solution is poured into a container of 4000 mL capacity, and then cotton fabric is soaked during 5 minutes ensuring it is completely wet. Then the fabric is centrifuged until it achieves 60% moisture content (calculated weight/weight). This 60% of moisture occluded represents a fabric or a matrix with a 3% of copper soaked.

As the fabric is centrifuged, the copper solution shall not migrate and homogeneous distribution is achieved.

It is allowed to evaporate or aerate up to 5% of the fabric moisture approximately (weight/weight). This is represented by the following chemical equilibrium:

$$Cu(NH_3)_4^{2+} + SO_4^{2-} + H_2O \rightleftharpoons CuSO_4 \cdot 4NH_3 \cdot H_2O_{(pp)}$$

Then temperature is applied to the fabric, according to the conditions of use desired for the matrix, one or both sides, this temperature should be about 60 to 120°, for a period of time that does not alter the physical qualities and fabric aesthetics to permeate, but to ensure the conversion of the reaction intermediate to alkaline copper sulphate occluded and fixed in the matrix.

This above mentioned formula is represented by the following chemical equilibrium:

$$4CuSO_4 \cdot 4NH_3 \cdot H_2O + 5H_2O \xrightarrow{\Delta} Cu_4SO_4(OH)_{6(pp)} + 3SO_4(NH_4)_{2(soluble)} + 10NH_{3(g)}$$

After performing the above steps, the material used shall have become a raw matrix with alkaline copper sulphate occluded and fixed with antibacterial properties, which then should follow the common steps of washing, dyeing and standardized routine processes of this type of material.

Finally, with normal washing, any soluble residue is removed leaving only the alkaline copper sulphate in the fabric:

$$Cu_4SO_4(OH)_{6(insoluble)} + 3SO_4(NH_4)_{2(soluble)} \xrightarrow{lavado} Cu_4SO_4(OH)_{6(insoluble)}$$

Example 2: Antibacterial Effect of the Compounds of Copper Oxide (I) Oxide, Copper Oxide (II), Copper Hydroxyphosphate (II), Copper Oxychloride (II) Upon 12 Bacterial Strains In this example, it was determined and compared the antibacterial activity of four chemical compounds. To this they were made 5 mm filter paper discs embedded with various concentrations of the compound oxide of copper (I), oxide copper (II), copper hydroxyphosphate (II), copper oxychloride (II) dissolved in DMSO (0 µg, 200 µg, 400 µg, 600 µg, 800 µg). The disks were deposited on a background lawn, which was performed as follows:

From a bacterial culture of 16 hours, with the strain of interest, it was performed a 1/30 dilution of the culture with fresh medium and incubated under stirring at 37° C. until reaching the exponential growth phase (D0600 nm 0.4-0.5). It was taken an aliquot of 100 µL of the culture in exponential phase, and deposited in 4 mL of Mueller-Hinton soft agar at 0.8% (previously melted and stabilized at 50° C.). The mixture was deposited on a Petri dish with 20 mL of Mueller-Hinton agar base. Once the agar was gelled, each of the discs with different amounts of the test compound were deposited on the background lawn, and incubated at 37° C. during 48 hairs.

Experiments were performed in triplicate in three independent events, using as negative control discs with the solvent DMSO alone, and as positive control were used commercial discs used with 30 µg of antibiotic Kanamycin (Km).

In Tables 1, 2, 3 and 4, you shall find the summary of the halo sizes of growth inhibition halo (mm) of 12 bacterial strains cultures when exposed to discs with different concentrations of compounds: copper oxide (I), copper oxide (II), copper hydroxyphosphate (II), copper oxychloride (II). In addition, each table gives details of inhibition halos of the controls.

The results indicate that the compounds oxide copper (I) oxide and copper (II) have no antibacterial activity on strains tested at the time evaluated at the concentrations used (Table 1 and Table 2). The copper hydroxyphosphate compound (II) has antibacterial activity only on the bacteria *Staphylococcus epidermidis* and *Streptococcus pyogenes* at the highest amount evaluated of 800 µg. Also, it presents growth inhibition activity on *Acinetobacter baumanii* in the range of 400 to 800 µg (Table 3). Meanwhile, copper oxychloride compound (II) has antibacterial activity against *Staphylococcus aureus, Staphylococcus epidermidis, Streptococcus pyogenes, Escherichia coli* and *Acinetobacter baumannii* (Table 4).

TABLE 1

Determination of the antibacterial activity of the compound oxide of copper (I)

| | Growth inhibition zone (naxn.) | | | | | |
|---|---|---|---|---|---|---|
| | Copper oxide compound (I) | | | | Controls | |
| Bacteria | 200 µg | 400 µg | 600 µg | 800 µg | Km | Disc DMSO |
| *Staphylococcus aureus* ATCC25923 | 5.0 | 5.0 | 5.0 | 5.0 | 21 ± 2 | 5.0 |
| *Staphylococcus epidermidis* ATCC25923 | 5.0 | 5.0 | 5.0 | 5.0 | 16 + 0.5 | 5.0 |
| *Streptococcus pneumoniae* ATCC14325 | 5.0 | 5.0 | 5.0 | 5.0 | 15 ± 0.8 | 5.0 |
| *Streptococcus pyogenes* ATCC2367 | 5.0 | 5.0 | 5.0 | 5.0 | 5 | 5.0 |
| *Enterococcus faecium* ISP133/04 | 5.0 | 5.0 | 5.0 | 5.0 | 12.5 ± 1.2 | 5.0 |
| *Enterococcus faecalis* ATCC29212 | 5.0 | 5.0 | 5.0 | 5.0 | 10 | 5.0 |
| *Escherichia coli* ATCC25922 | 5.0 | 5.0 | 5.0 | 5.0 | 18 ± 1.8 | 5.0 |
| *Klebsiella pneumoniae* ATCC4352 | 5.0 | 5.0 | 5.0 | 5.0 | 19 ± 0.3 | 5.0 |
| *Pseudomonas aeruginosa* PAOI | 5.0 | 5.0 | 5.0 | 5.0 | 7 ± 1.0 | 5.0 |
| *Acinetobacter baumanii* UBP456 | 5.0 | 5.0 | 5.0 | 5.0 | 5.0 | 5.0 |
| *Citrobacter freundii* ISP1949/99 | 5.0 | 5.0 | 5.0 | 5.0 | 19 ± 0.3 | 5.0 |
| *Enterobacter aerogenes* ATCC13048 | 5.0 | 5.0 | 5.0 | 5.0 | 14 + 0.5 | 5.0 |

TABLE 2

Determination of the antibacterial activity of the compound oxide of copper (II)

| | Growth inhibition zone (mi) | | | | | |
|---|---|---|---|---|---|---|
| | Copper oxide compound (II) | | | | Controls | |
| Bacteria | 200 µg | 400 µg | 600 µg | 800 µg | Km | Disc DMSO |
| *Staphylococcus Aureus* ATCC25923 | 5.0 | 5.0 | 5.0 | 5.0 | 20 ± 0.8 | 5.0 |
| *Staphylococcus epidennidis* ATCC25923 | 5.0 | 5.0 | 5.0 | 5.0 | 14 + 0.7 | 5.0 |
| *Streptococcus pneumoniae* ATCC14325 | 5.0 | 5.0 | 5.0 | 5.0 | 12.5 ± 1.2 | 5.0 |
| *Streptococcus pyogenes* ATCC2367 | 5.0 | 5.0 | 5.0 | 5.0 | 5.0 | 5.0 |
| *Enterococcus faecium* ISP133/04 | 5.0 | 5.0 | 5.0 | 5.0 | 9 ± 0.7 | 5.0 |
| *Enterococcus Faecalis* ATCC29212 | 0.5 | 5.0 | 5.0 | 5.0 | 15 + 0.6 | 5.0 |
| *Escherichia coli* ATCC25922 | 5.0 | 5.0 | 5.0 | 5.0 | 15 ± 0.2 | 5.0 |
| *Klebsiella pneumoniae* ATCC4352 | 5.0 | 5.0 | 5.0 | 5.0 | 11 ± 1 | 5.0 |
| *Pseudomonas Aeruginosa* PAOI | 5.0 | 5.0 | 5.0 | 5.0 | 9 ± 0.7 | 5.0 |
| *Acinetobacter baumanii* UDP456 | 5.0 | 5.0 | 5.0 | 5.0 | 5.0 | 5.0 |
| *Citrobacter freundii* ISP1949/99 | 5.0 | 5.0 | 5.0 | 5.0 | 12 ± 0.5 | 5.0 |
| *Enterobacter aerogenes* ATCC13048 | 5.0 | 5.0 | 5.0 | 5.0 | 15 ± 0.4 | 5.0 |

TABLE 3

Determination of the antibacterial activity of copper hydroxyphosphate compound (II)

| | Growth inhibition zone (mm) | | | | | |
|---|---|---|---|---|---|---|
| | Copper hydroxyphosphate compound (II) | | | | Controls | |
| Bacteria | 200 µg | 400 µg | 600 µg | 800 µg | Km | Disc DMSO |
| Staphylococcus aureus ATCC25923 | 5.0 | 5.0 | 5.0 | 5.0 | 15 ± 0.5 | 5.0 |
| Staphylococcus epidermidis ATCC25923 | 5.0 | 5.0 | 5.6 ± 0.5 | 6.3 ± 1.1 | 18 ± 0.7 | 5.0 |
| Streptococcus pneumoniae ATCC14325 | 5.0 | 5.0 | 5.0 | 5.0 | 11 ± 1 | 5.0 |
| Streptococcus pytogenes ATCC2367 | 5.0 | 5.0 | 5.0 | 8.6 ± 0.6 | 5.0 | 5.0 |
| Enterococcus faecium ISP133/04 | 5.0 | 5.0 | 5.0 | 5.0 | 9 ± 0.7 | 5.0 |
| Enterococcus faecalis ATCC29212 | 5.0 | 5.0 | 5.0 | 5.0 | 15 ± 0.6 | 5.0 |
| Escherichia coli ATCC25S22 | 5.0 | 5.0 | 5.0 | 5.0 | 18 ± 0.7 | 5.0 |
| Klebsiella pneumoniae ATCC4352 | 5.0 | 5.0 | 5.0 | 5.0 | 11 ± 1 | 5.0 |
| Pseudomonas Aeruginosa PAO1 | 5.0 | 5.0 | 5.0 | 5.0 | 7 + 0.7 | 5.0 |
| Acinetobacter baumanii UDP456 | 5.0 | 8.6 ± 0.6 | 7.3 ± 2 | 7.6 ± 2.3 | 5.0 | 5.0 |
| Citrobacter fraundii ISP1949/99 | 5.0 | 5.0 | 5.0 | 5.0 | 15 ± 0.5 | 5.0 |
| Enterobacter aeroffenes ATCC13048 | 5.0 | 5.0 | 5.0 | 5.0 | 16 ± 0.4 | 5.0 |

TABLE 4

Determination of the antibacterial activity of copper oxychloride compound (II).

| | Growth inhibition zone <mm) | | | | | | | |
|---|---|---|---|---|---|---|---|---|
| | Compound | | | | | Controls | | |
| Bacteria | 200 µg | 400 µg | 600 µg | 800 µg | Fabric with | Km | Disc DMSO | Fabric without |
| Staphylococcus aureus ATCC25923 | 6.0 ± 1.0 | 10.3 ± 0.6 | 11.7 ± 0.6 | 14.0 ± 1.0 | 29.0 ± 1.0 | 19.0 | 5.0 | 20.0 |
| Staphylococcus epidermidis ATCC25923 | 12.0 ± 0.6 | 14.3 ± 0.6 | 13.7 ± 1.5 | 14.6 ± 0.6 | 30.3 ± 2.3 | 18.5 ± 3.5 | 5.0 | 20.0 |
| Straptococus pneumoniae ATCC14325 | 5.0 ± 1.0 | 8.0 ± 0.7 | 9.0 ± 1.0 | 11.0 ± 1.2 | 28.0 ± 0.4 | 11.5 ± 0.8 | 5.0 | 20.0 |
| Streptococcus pyogenes ATCC2367 | 5.0 ± 1.0 | 6.0 ± 1.0 | 7.0 ± 1.2 | 8.0 ± 1.4 | 28.0 ± 0.4 | 5.0 | 5.0 | 20.0 |
| Enterococcus faecium ISP133/04 | 6.0 ± 1.0 | 6.0 + 1.0 | 6.0 ± 1.0 | 6.0 ± 1.0 | 25.0 | 11.0 | 5.0 | 20.0 |
| Enterococcus faecalis ATCC29212 | 6.0 ± 1.0 | 6.0 ± 1.0 | 6.0 ± 1.0 | 6.0 ± 1.0 | 25.0 | 10.5 ± 0.2 | 5.0 | 20.0 |
| Escherichia coli ATCC25S22 | 13.3 ± 1.4 | 13.0 ± 0.7 | 15.0 ± 0.7 | 13.3 ± 0.7 | 31.7 ± 2.1 | 20.0 ± 0.7 | 5.0 | 20.0 |
| Klebsiella pneumoniae ATCC4352 | 7.3 ± 0.6 | 8.7 ± 0.6 | 9.7 ± 0.6 | 10.0 | 29.0 ± 1.0 | 5.0 | 5.0 | 20.0 |
| Pseudomonas aeruginosa PAOI | 6.3 ± 1.5 | 6.7 ± 1.2 | 8.3 ± 0.6 | 3.3 ± 1.7 | 23.0 ± 1.0 | 7.0 ± 1.4 | 5.0 | 20.0 |
| Acinetobacter baumanii UDP456 | 11.7 ± 0.6 | 15.7 ± 0.6 | 17.0 ± 1.0 | 19.7 ± 0.6 | 32.0 ± 3.5 | 16.0 ± 1.4 | 5.0 | 20.0 |
| Citrobacter freundii ISP1949/99 | 8.0 ± 1.0 | 10.7 ± 1.5 | 11.3 ± 0.6 | 11.3 ± 1.5 | 30.3 ± 1.2 | 19.0 ± 0.2 | 5.0 | 20.0 |
| Enterobacter aerogenes ATCC13048 | 7.3 ± 1.5 | 3.7 ± 1.5 | 9.7 ± 0.6 | 9.7 ± 1.5 | 27.7 ± 0.6 | 19.0 ± 0.7 | 5.0 | 20.0 |

Example 3: Antibacterial Effect of a Thin Cloth Soaked with Compound $Cu_4SO_4(OH)_6$ (Alkaline Copper Sulfate)

In this example, the antimicrobial activity of the invention was determined by testing on sensidiscs. On order to do this, they were prepared 5 mm filter paper discs, embedded with various concentrations of compound $Cu_4SO_4(OH)_6$ (Alkaline Copper Sulfate) of the study dissolved in DMSO (0 µg, 200 µg, 400 µg, 600 µg, 800 µg). In addition, pieces of cloth of about 2×2 cm were prepared and embedded with the new product. Paper discs and fabric were deposited on a background lawn, which was performed as follows:

From a bacterial culture of 16 hours, with the strain of interest, it was performed a 1/30 dilution of the culture with fresh medium and incubated under stirring at 37° C. until reaching the exponential growth phase (D0600 nm 0.4-0.5). It was taken an aliquot of 100 μL of the culture in exponential phase, and deposited in 4 mL of Mueller-Hinton soft agar at 0.8% (previously melted and stabilized at 50° C.). The mixture was deposited on a Petri dish with 20 mL of Mueller-Hinton agar base. Once the agar was gelled, each of the discs with different amounts of the test compound were deposited on the background lawn, and incubated at 37° C. during 48 hours.

Experiments were performed in triplicate in independently, using as negative control discs with the solvent DMSO alone and cloth without the product of study. As positive control were used commercial discs used with 30 μg of antibiotic Kanamycin (Km). The results are presented in Table 5.

The compound Alkaline Copper Sulfate $(OH)_6$ presents antibacterial activity on all bacterial strains tested (Table 5). Finally, if the proposed invention is compared with the 4 chemical compounds of Example 2, copper oxide (I) cooper oxide (II), copper hydroxyphosphate (II), copper oxychloride (II), the product of invention exhibits a spectrum of antibacterial activity greater than the hydroxyphosphate copper compounds (II) and copper oxychloride (II).

formed in the JSM-5410 Scanning Microscopic equipment and it was used Vantage 1.4.2 software to analyze the results. The samples were coated with Au—Pd bath.

Figure 2:
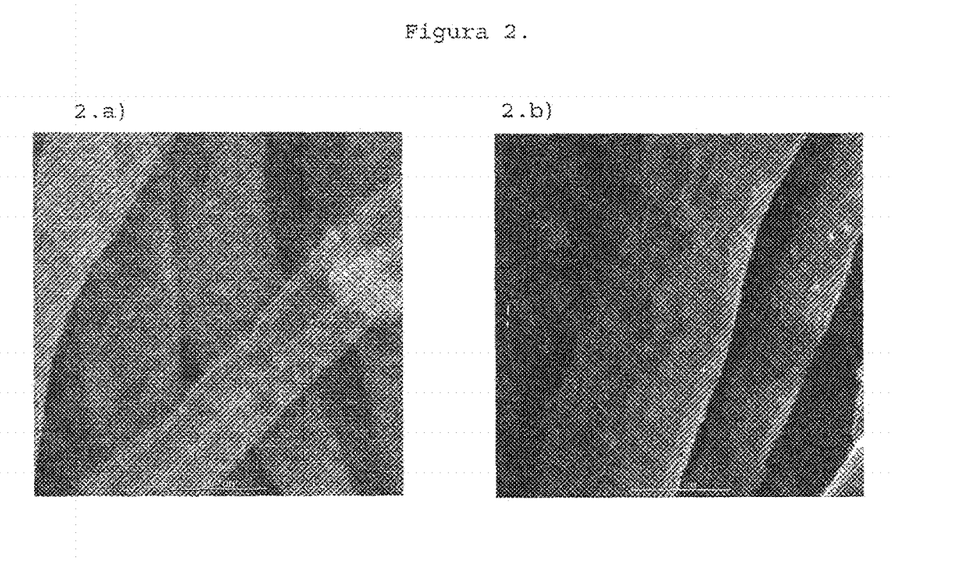
FIG. 2.—Petrographies of electronic scanning electron microscopy of control fabric and fabric impregnated with the antibacterial compound increased at 16 μt. In a), it is observed the control material at the increase described. In b), it is shown the image of the occluded material, fixed, and impregnated with the proposed compound by the inventor. It is noted the presence of copper incorporation into the proposed fabric.

By comparing the images of the fabric with the embedded compound (FIG. 1a) and the control fabric (FIG. 1b), it is noted that the fabric with the compound has noticeably brighter areas than the control fabric, which correspond to parts of the structure with higher molecular weight due to the presence of the compound. Additionally, it is noted that the alkaline copper solution applied to the fabric is impregnated homogeneously within it, leaving some insoluble residues. By observing the the fabric impregnated with the compound at a higher magnification (FIG. 2b), it is observed the presence of copper incorporated into the fiber.

Figure 3:
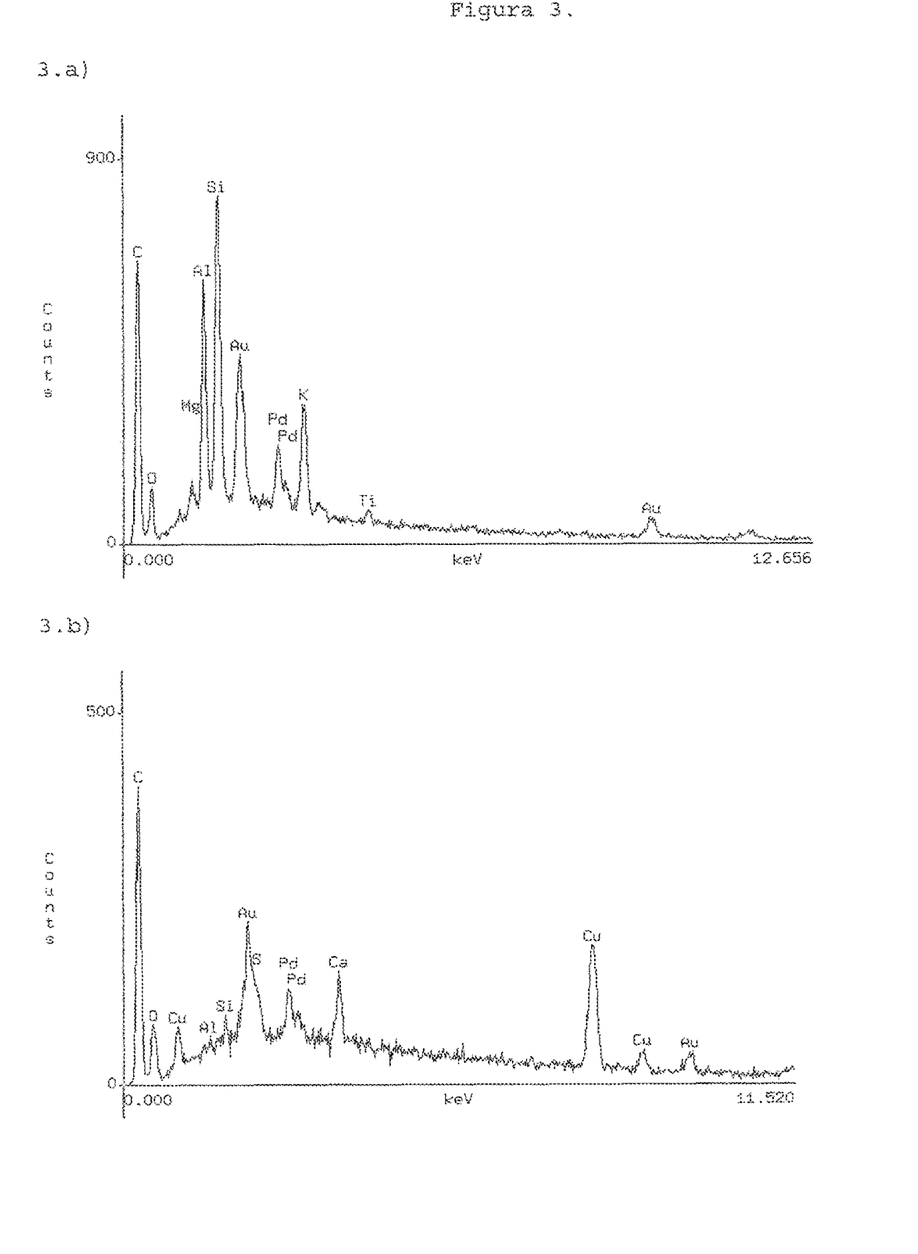
FIG. 3.—Graphic of the scanning microscopy of the control fabric and the fabric with the proposed compound incorporated. The analysis peaks represent the presence and abundance of atoms analyzed and specified on it. The presence of copper in the fabric is verified.

The analysis of the composition of the control fabric determined the presence of oxygen, aluminum, silicon atoms, finding further traces of magnesium, potassium and titanium (FIG. 3a). Meanwhile, the analysis of the fabric impregnated with the compound shows the presence of a high copper content, the presence of oxygen, aluminum and traces of calcium (FIG. 3b). Traces of water may be due to calcium in the applied solution.

TABLE 5

Antibacterial activity of thin cloth soaked with the proposed compound (Alkaline Copper Sulphate)

| | Growth inhibition zone (ram.) | | | | | | | |
|---|---|---|---|---|---|---|---|---|
| | Compound | | | | | Controls | | |
| Bacteria | 200 μg | 400 μg | 600 μg | 800 μg | Fabric with comp | Km | Disc DMSO | Fabric without comp |
| *Staphylococcus aureus* ATCC25923 | 6.0 ± 1.0 | 10.3 ± 0.6 | 11.7 ± 0.6 | 14.0 ± 1.0 | 29.0 ± 1.0 | 19.0 | 5.0 | 20.0 |
| *Staphylococcus epidermidis* ATCC25923 | 12.0 ± 0.6 | 14.3 ± 0.6 | 13.7 ± 1.5 | 14.6 ± 0.6 | 30.3 ± 2.3 | 18.5 ± 3.5 | 5.0 | 20.0 |
| *Streptococcus pneumonia* ATCC14325 | 5.0 ± 1.0 | 8.0 ± 0.7 | 9.0 ± 1.0 | 11.0 ± 1.2 | 28.0 ± 0.4 | 11.5 ± 0.8 | 5.0 | 20.0 |
| *Streptococcus pyogenes* ATCC2367 | 5.0 ± 1.0 | 6.0 ± 1.0 | 7.0 ± 1.2 | 8.0 ± 1.4 | 28.0 ± 0.4 | 5.0 | 5.0 | 20.0 |
| *Enterococcus faecium* ISP133/04 | 6.0 ± 1.0 | 6.0 ± 1.0 | 6.0 ± 1.0 | 6.0 ± 1.0 | 25.0 | 11.0 | 5.0 | 20.0 |
| *Enterococcus faecalis* ATCC29212 | 6.0 ± 1.0 | 6.0 ± 1.0 | 6.0 ± 1.0 | 6.0 ± 1.0 | 25.0 | 10.5 ± 0.2 | 5.0 | 20.0 |
| *Escherichia coli* ATCC25922 | 13.3 ± 1.4 | 13.0 ± 0.7 | 15.0 ± 0.7 | 13.3 ± 0.7 | 31.7 ± 2.1 | 20.0 ± 0.7 | 5.0 | 20.0 |
| *Klebsiella pneumoniae* ATCC4352 | 7.3 ± 0.6 | 8.7 ± 0.6 | 9.7 ± 0.6 | 10.0 | 29.0 ± 1.0 | 5.0 | 5.0 | 20.0 |
| *Pseudomonas aeruginosa* PAOI | 6.3 ± 1.5 | 6.7 ± 1.2 | 8.3 ± 0.6 | 8.3 ± 1.7 | 23.0 ± 1.0 | 7.0 ± 1.4 | 5.0 | 20.0 |
| *Acinetobacter baumannii* UDP456 | 11.7 ± 0.6 | 15.7 ± 0.6 | 17.0 ± 1.0 | 19.7 ± 0.6 | 32.0 ± 3.5 | 16.0 + 1.4 | 5.0 | 20.0 |
| *Citrobacter freundii* ISP1949/99 | 8.0 ± 1.0 | 10.7 ± 1.5 | 11.3 ± 0.6 | 11.3 ± 1.5 | 30.3 ± 1.2 | 19.0 ± 0.2 | 5.0 | 20.0 |
| *Enterobacter aerogenes* ATCC13048 | 7.3 ± 1.5 | 9.7 ± 1.5 | 9.7 ± 0.6 | 9.7 ± 1.5 | 27.7 ± 0.6 | 19.0 ± 0.7 | 5.0 | 20.0 |

Example 4: Electronic Scanning Microscopy for a Matrix of Fabric with Antimicrobial Activity In this example, the fabric structure was compared with the compound of alkaline copper occluded, fixed and embedded and the control fabric (no compound) using electronic scanning microscopy. The analysis was per- Example 5: Quantitative Analysis of the Antibacterial Activity of the Matrix (Thick Cloth) Occluded and Fixed with Alkaline Copper Sulphate In this example, the antibacterial activity was quantitatively established of a thick or heavy cloth, which was treated by the process of the present invention for fixing and occlusion of alkaline copper sulfate, upon bacterial strains of

*Staphylococcus aureus* ATCC 25923 and *Escherichia coli* ATCC 25322, from tests determining the minimum inhibitory concentration (MIC). From a bacterial culture of 16 hours, with the strain of interest, it was performed a 1/30 dilution of the culture with fresh medium and incubated under stirring at 37° C. until reaching the exponential growth phase (D0600 nm 0.4-0.5). It was taken an aliquot of 100 μL of the culture in exponential phase, and deposited in 4 mL of Mueller-Hinton soft agar at 0.8% (previously melted and stabilized at 50° C.). The mixture was deposited on a Petri dish with 20 mL of Mueller-Hinton agar base. Once the agar was gelled, then an E-test generated with a concentration gradient of the study compound was deposited on the background lawn, and incubated at 37° C. during 48 hours.

Experiments were performed in triplicate in three independent events, using as negative control discs with dimethyl sulfoxide solvent (DMSO) alone and as positive control were used commercial discs used with 30 μg of antibiotic Kanamycin (Km).

The results of the minimum inhibitory concentration (Table 6) indicate that compound of alkaline copper sulphate fixed and occluded in a heavy fabric presents antibacterial activity, which is reflected in a minimum inhibitory concentration of 200 ug/mL for bacteria *Staphylococcus aureus* ATCC 25923 and 300 ug/mL for *Escherichia coli* ATCC 25922).

TABLE 6

Minimum Inhibitory Concentration of copper solution occluded and fixed in a thick cloth

| Bacteria | MIC | DMSO | Kanamycin |
|---|---|---|---|
| *Staphylococcus aureus* ATCC 25923 | 200 μg/mL | – | + |
| *Escherichia coli* ATCC 25922 | 300 μg/mL | – | + |

Example 6: Qualitative Determination of the Antibacterial Activity of the Matrix (Thick Cloth) Occluded and Fixed with Alkaline Copper Sulphate This example determined qualitatively the antibacterial effect of the copper solution proposed, embedded in a matrix of thick fabric which was prepared following the procedure of the present invention. Pieces of cloth of about 2×2 cm were prepared and embedded with the product and then were deposited on a background lawn of 12 different bacteria strains.

In order to do this, it was prepared a bacterial culture of 16 hours, with the strain of interest, it was performed a 1/30 dilution of the culture with fresh medium and incubated under stirring at 37° C. until reaching the exponential growth phase (D0600 nm 0.4-0.5). It was taken an aliquot of 100 μL of the culture in exponential phase, and deposited in 4 mL of Mueller-Hinton soft agar at 0.8% (previously melted and stabilized at 50° C.). The mixture was deposited on a Petri dish with 20 mL of Mueller-Hinton agar base. Once the agar was gelled, each of the discs with different amounts of the test compound were deposited on the background lawn, and incubated at 37° C. during 48 hours.

Experiments were performed in triplicate in independently, using as negative control discs with the solvent DMSO alone and cloth without the product of study. As positive control were used commercial discs used with 30 μg of antibiotic Kanamycin (Km).

Experiments were performed in triplicate in three independent events. The results obtained (Table 7) indicate that the proposed solution of copper mounted on a thicker fabric matrix presents antibacterial activity on almost all bacterial strains tested.

TABLE 7

Antibacterial activity of matrix (thick cloth) occluded and fixed with alkaline copper sulphate

| | Growth inhibition zone | | |
|---|---|---|---|
| Bacteria | Fabric with comp | Fabric without | Km |
| *Staphylococcus aureus* ATCC25923 | 28.3 ± 0.7 | 20 | 18.0 ± 0.5 |
| *Staphylococcus epidermidis* ATCC2S923 | 29.3 ± 1.7 | 20 | 24.0 ± 1.0 |
| *Streptococcus pneumoniae* ATCC14325 | 26.3 ± 0.6 | 20 | 10.0 ± 0.2 |
| *Streptococcus pyogenes* ATCC2367 | 26.0 ± 1.0 | 20 | 6.0 ± 1.0 |
| *Enterococcus faecium* ISP133/04 | 23.3 + 0.6 | 20 | 11.0 ± 0.8 |
| *Enterococcus faecalis* ATCC29212 | 25.6 ± 0.7 | 20 | 14.0 ± 1.0 |
| *Escherichia coli* ATCC25922 | 24.6 ± 0.6 | 20 | 19.0 ± 0.5 |
| *Klebsiella pneumoniae* ATCC4352 | 27.0 ± 0.6 | 20 | 18.0 ± 1.0 |
| *Pseudomonas aeruginosa* PAOI | 23.0 ± 0.7 | 20 | 7.0 ± 0.5 |
| *Acinetobacter baumanii* UPP4 56 | 26.3 ± 0.3 | 20 | 5.0 |
| *Citrobacter freundii* ISP1949/99 | 23.3 ± 0.3 | 20 | 17.0 + 0.3 |
| *Enterobacter aerogenes* ATCC13048 | 24.0 ± 1.0 | 20 | 12.0 ± 0.5 |

From the above examples, it can be indicated that the maximum and minimum concentrations for inclusion into the matrix and required for said matrix having antimicrobial effect, can be in the range of about 0.1% to about 5% of active copper (in relation to the weight of the matrix), which is relevant, because it has activity with a low concentration of copper. Higher concentrations of active copper would be unnecessary to achieve the proposed antibacterial effect.

Example 7: Conversation of the Antimicrobial Activity of the Matrixes in Thick and Thin Fabrics Containing Alkaline Copper Sulphate Occluded and Fixed, after Washing This example established qualitatively the antibacterial activity of matrixes in thin fabric (Fabric 1) and thick fabric (Fabric 2) embedded with the product, following the procedure described herein, and after subjected to washing. In order to do this, there were taken pieces of 2×2 cm from both fabrics, cut and washed for 2 hours with stirring using commercial laundry detergent. Subsequently, the washed fabric pieces which have the new product are dried in an oven at 40° C. for 3 hours and placed on the background lawn. In order to generate the background lawn, it was prepared a bacterial culture of 16 hours, with the strain of interest, it was performed a 1/30 dilution of the culture with fresh medium and incubated under stirring at 37° C. until reaching the exponential growth phase (D0600 nm 0.4-0.5). It was taken an aliquot of 100 μL of the culture in exponential phase, and deposited in 4 mL of Mueller-Hinton soft agar at 0.8% (previously melted and stabilized at 50° C.). The mature was deposited on a Petri dish with 20 mL of Mueller-Hinton agar base. Once the agar was gelled, each of the discs with the different amounts of the compound were deposited on the background lawn, and incubated at 37° C. during 48 hours.

Experiments were performed using as negative control pieces of both fabrics without the product of study and undergoing the process before mentioned. Additionally, as positive control, they were used commercial discs used with 30 μg of antibiotic Kanamycin (Km).

Experiments were performed in triplicate and in three independent events. From the treated plates, it was measured the zone of inhibition generated by each control and fabrics embedded with the proposed compound, which is summarized in Table 7. It was noted that both the thin fabric (Fabric 1) and the thick fabric (Fabric 2) impregnated with copper proposed solution, maintain their antibacterial activity on the two strains evaluated after being washed with a commercial detergent.

TABLE 8

Determination of the inhibition halos of thin fabric (Fabric 1) and thick fabric (Fabric 2) with alkaline copper sulphate occluded and fixed.

| Bacteria | Growth inhibition zone | | | | |
| --- | --- | --- | --- | --- | --- |
| | Fabric 1 with comp | Fabric 1 without comp | Fabric 2 with comp | Fabric 2 without comp | Km |
| Staphylococcus aureus ATCC25923 | 27 ± 1.7 | 20 | 26.0 ± 1.0 | 20 | 18.0 ± 1.4 |
| Escherichia coli ATCC25922 | 24 ± 1.7 | 20 | 16.3 ± 1.2 | 2.0 | 20.6 ± 0.6 |

The invention claimed is:

1. A method of impregnating an active compound into a vegetable, animal, synthetic origin matrix, or mixtures of two or more thereof, said method comprising:
   a) Absorbing or impregnating a preliminary compound into said matrix;
   b) Spinning, pressing, or crushing of said matrix;
   c) Exposing said matrix to air; and
   d) Fixing and obtaining the active compound in said matrix.

2. The method according to claim 1, wherein the preliminary compound comprises a solution of copper sulfate pentahydrate with liquid or gaseous ammonia.

3. The method according to claim 1, wherein the step of spinning pressing, or crushing comprises removing, by any mechanical means, the aqueous surplus of formulated copper with ammonia for end use of the matrix.

4. The method according to claim 1, wherein the step of exposing said matrix to air comprises evaporating an exceeding aqueous solvent of the formulated leaving an intermediate compound $CuSO_4 \cdot 4NH_3 \cdot H_2O$, keeping the uniform and homogeneous distribution of copper in the matrix to avoid having localized and uncontrolled migration.

5. The method according to claim 1, wherein a matrix with strong antimicrobial properties is prepared.

6. The method according to claim 1, wherein the step of fixing and obtaining the active compound comprises applying a temperature between 50° C. and 120° C. to the matrix.

7. The method according to claim 6, wherein the step of fixing and obtaining the active compound comprises obtaining an active compound of alkaline copper sulfate and achieving adhesion of the active compound to the matrix with uniform distribution.

8. The method according to claim 1, wherein the active compound is distributed uniformly in the matrix with a concentration gradient from one side of the matrix to another.

9. The method according to claim 1, wherein the active compound is distributed uniformly in the matrix with different concentration gradients.

10. The method according to claim 5, further comprising a step of washing, wherein the matrix maintains its antimicrobial properties after being washed.

11. The method according to claim 7, wherein said matrix, after the step of fixing and obtaining the active compound, comprises between about 0.1% and about 5% of active copper, expressed as elemental copper based on the weight of the matrix.

* * * * *